(12) United States Patent
Choi et al.

(10) Patent No.: US 8,722,098 B2
(45) Date of Patent: May 13, 2014

(54) ECKLONIA CAVA EXTRACTS FOR ALLEVIATING OR PREVENTING ASTHMATIC REACTIONS

(75) Inventors: Il-Whan Choi, Busan (KR); Da-Young Lee, Busan (KR); Inhak Choi, Busan (KR); Se-Kwon Kim, Busan (KR); Won-Kyo Jung, Busan (KR); Sung Su Yea, Busan (KR); Yung Hyun Choi, Busan (KR)

(73) Assignee: Pukyong National University Industry-Academic Cooperation, Busan (KR)

( * ) Notice: Subject to any disclaimer, the term of this patent is extended or adjusted under 35 U.S.C. 154(b) by 669 days.

(21) Appl. No.: 11/851,359

(22) Filed: Sep. 6, 2007

(65) Prior Publication Data

US 2009/0068265 A1    Mar. 12, 2009

(51) Int. Cl.
*A61K 35/20*     (2006.01)
*A61K 35/24*     (2006.01)
*A61K 35/37*     (2006.01)
*A61K 36/03*     (2006.01)

(52) U.S. Cl.
CPC ..................................... *A61K 36/03* (2013.01)
USPC ....................................................... 424/535

(58) Field of Classification Search
None
See application file for complete search history.

(56) References Cited

U.S. PATENT DOCUMENTS 6,774,145 B1    8/2004    Lee et al.

FOREIGN PATENT DOCUMENTS

| JP | 56148245 A | * | 11/1981 |
| JP | 08092103 A | * | 4/1996 |
| JP | 11021247 A | * | 1/1999 |
| JP | 2002223727 A | * | 8/2002 |
| JP | 2006022033 A | * | 1/2006 |

OTHER PUBLICATIONS

Persson. "Mice Are Not a Good Model of Human Airway Disease". Amer. J. Respiratory and Critical Care Medicine. vol. 166 (2002) 6-7.*
Jung et al. "Blockade of airway hyperresponsiveness and inflammation in a murine model of asthma by *Ecklonia cava* ethanolic extracts". Abstracts of Papers, 232nd ACS National Meeting, San Francisco, CA. (Sep. 10-14, 2006).*
KF Chung and SR Durham. Asthma as an inflammatory disease: Clinical perspectives. British Medical Bulletin vol. 48 (1992) 179-189. Abstract only.*
Feltis et al. Increased Vascular Endothelial Growth Factor and Receptors: Relationship to Angiogenesis in Asthma. American Journal of Respiratory and Critical Care Medicine vol. 173 (2006) 1201-1207.*
(U1) "Solubility". Internet Archive Date: Jul. 17, 2011 [Retrieved from the Internet on: Jun. 14, 2013]. Retrieved from: <URL: http://www.chem.wisc.edu/deptfiles/genchem/sstutorial/Text11/Tx112/tx112.html>.*
Kim, Se-Kwon, Da-Young Lee, Won-Kyo Jung, Ji-Hye Kim, Inhak Choi, Sae-Gwang Park, Su-Kil Seo, Soo-Woong Lee, Chang Min Lee, Sung Su Yea, Yung Hyun Choi, and Il-Whan Choi. Effects of *Ecklonia cava* ethanolic extracts on airway hyperresonsiveness and inflammation in a marine asthme model: Role of Suppressor of cytokine signaling. Biomedicine & Pharmacotherapy. 62 (pp. 289-296). [Online] Aug. 10, 2007.
P.M. Yao, et al.; "Divergent regulation of 92-kDa gelatinase and TIMP-1 by HBECs in response to IL-1β and TNF-α"; The American Physiological Society, 1997, pp. L866-L874.
Gisèle Mautino, et al.; "Increased Release of Matrix Metlloproteinase-9 in Bronchoalveolar Lavage Fluid and by Alveolar Macrophages of Asthmatics", Am. J. Respir. Cell Mol. Biol., vol. 17, pp. 583-591, 1997.
David Leppert, et al.; "T Cell Gelatinases Mediate Basement Membrane Transmigration in Vitro[1]"; The American Association of Immunologists; 1995, pp. 4379-4389.
Christophe Delclaux, et al., "Role of Gelatinase B and Elastase in Human Polymorphonuclear Neutrophil Migration across Basement Membrane", Am. J. Respir. Cell Mol. Biol., vol. 14, pp. 288-295, 1996.
Martin Illemann, et al., "MMP-9 Is Differentially Expressed in Primary Human Colorectal Adenocarcinomas and Their Metastases", Mol. Cancer Res. 2006; 4(5), May 2006, pp. 293-302.
Antonio M. Vignola, et al., "Sputum Metalloproteinase-9/Tissue Inhibitor of Metalloproteinase-1 Ratio Correlates with Airflow Obstruction in Asthma and Chronic Bronchitis", Am. J. Respir. Crit Care Med., vol. 158., pp. 1945-1950, 1998.
Makoto Hoshino, et al., "Inhaled corticosteroids decrease subepithelial collagen deposition by modulation of the balance between matrix metalloproteinase-9 and tissue inhibitor of metalloproteinase-1 expression in asthma", J. Allergy Clin Immunol, vol. 104, No. 2, Part 1, pp. 356-363. 1999.
Jodie L. Simpson, et al., "Differential Proteolytic Enzyme Activity in Eosinophilic and Neutrophilic Asthma", American Journal of Respiratory and Critical Care Medicine, vol. 172, 2005, pp. 559-565.
Minoru Fujimoto, et al, "Regulation of cytokine signaling by SOCS family molecules", Trends in Immunology, vol. 24, No. 12, Dec. 2003, pp. 659-666.
Hiroyuki Ohbayashi, et al., "Matrix Metalloproteinase-9 and Airway Remodeling in Asthma", Current Drug Targets—Inflammation & Allergy, 2005, 4, pp. 177- 181.

(Continued)

*Primary Examiner* — Amy L Clark
(74) *Attorney, Agent, or Firm* — Steptoe & Johnson LLP (57) ABSTRACT

A method of alleviating or preventing inflammation in an animal is provided. In concrete, the method comprises the step of administering to an animal a composition including an *Ecklonia cava* extract in an amount effective to suppress SOCS-3 expression in the animal to thereby alleviate or prevent inflammation in the animal.

16 Claims, 8 Drawing Sheets

(56) References Cited

OTHER PUBLICATIONS

Masato Kubo, et al., "Suppressors of cytokine signaling and immunity", Nature Immunology, vol. 4, No. 12, Dec. 2003, pp. 1169-1176.

Yoh-ichi Seki, et al., "SOCS-3 regulates onset and maintenance of TH2-mediated allergic responses", Nature Medicine, vol. 9, No. 8, Aug. 2003, pp. 1047-1054.

Yoh-ichi Seki, et al., "Expression of the suppressor of cytokine signaling-5 (SOCS5) negatively regulates IL-4-dependent STAT6 activation and Th2 differentiation", PNAS, vol. 99, No. 20, Oct. 1, 2002, pp. 13003-13008, www.pnas.org/cgi/doi/10.1073/pnas.202477099.

Hye Sook Kang, et al., "Inhibitory Phlorotannins from the Edible Brown Alga *Ecklonia stolonifera* on Total Reactive Oxygen Species (ROS) Generation", Arch Pharm Res., vol. 27, No. 2, pp. 194-198, 2004.

Moon-Moo Kim, et al., "Phlorotannins in *Ecklonia cava* extract inhibit matrix metalloproteinase activity", Life Sciences, vol. 79, 2006, pp. 1436-1443.

Mi-Jeong Ahn, et al., "Inhibition of HIV-1 Reverse Transcriptase and Protease by Phlorotannins from the Brown Alga *Ecklonia cava*", Biol. Pharm. Bull. 27(4), 2004, pp. 544-547.

Hyeon-Cheol Shin, et al., "An Antioxidative and Antiinflammatory Agent for Potential Treatment of Osteoarthritis from *Ecklonia cava*", Arch Pharm Res. vol. 29, No. 2, 2006, pp. 165-171.

David H. Broide, MD, "Molecular and cellular mechanisms of allergic disease", Supplement to the Journal of Allergy and Clinical Immunology, vol. 108, No. 2, pp. S65-S71, Aug. 2001.

A. Tomkinson, et al., "A Murine IL-4 Receptor Antagonist That Inhibits IL-4- and IL-13-Induced Responses Prevents Antigen-Induced Airway Eosinophilia and Airway Hyperresponsiveness", The Journal of Immunology, 2001, 166, pp. 5792-5800.

Vipul V. Jain, et al., "CpG-oligodeoxynucleotides inhibit airway remodeling in a murine model of chronic asthma", J. Allergy Clin Immunol., Dec. 2002, pp. 867-872.

Hideaki Nagase, "Activation Mechanisms of Matrix Metalloproteinases", Biol. Chem., vol. 378, Mar./Apr. 1997, pp. 151-160.

Gillian Murphy, et al., "The Matrix Metalloproteinases and Their Inhibitors", American Journal of Respiratory Cell and Molecular Biology, vol. 7, pp. 120-125, 1992.

Harald Renz, et al., "T Cells Expressing Specific Vβ Elements Regulate Immunoglobulin E Productive and Airways Responsiveness in Vivo", J. Exp. Med., the Rockefeller University Press, vol. 177, Apr. 1993, pp. 1175-1180.

Marsha Wills-Karp, "Immunologic Basis of Antigen-Induced Airway Hyperresponsiveness", Annu. Rev. Immunol. 1999, 17:255-281.

Punnonen J, et al., "Role of interleukin-4 and interleukin-13 in synthesis of IgE and expression of CD23 by human B cells", Allergy 49, 576-586, 1994.

Hirohisa Saito, et al., "Selective differentiation and proliferation of hematopoietic cells induced by recombinant human interleukins", Proc. Natl. Acad. Sci, USA, vol. 85, pp. 2288-2292, Apr. 1988, Immunology.

Itsuo Iwamoto, et al., "Interfereon γ Regulates Antigen-induced Eosinophil Recruitment into the Mouse Airways by Inhibiting the Infiltration of CD4$^+$T Cells", J. Exp. Med., The Rockefeller University Press, vol. 177, Feb. 1993, pp. 573-576.

Robert A. Seder, et al., "The Presence of Interleukin 4 during In Vitro Priming Determines the Lymphokine-producing Potential of CD4$^+$ T Cells from the T Cell Receptor Transgenic Mice", The Journal of Experimental Medicine, vol. 176, Oct. 1992, pp. 1091-1098.

Manfred Kopf, et al., "Disruption of the murine IL-4 gene blocks Th2 cytokine responses", Nature, vol. 362, 18 Mar. 1993, pp. 245-248.

Lorna J. Wood, et al., "Changes in Bone Marrow Inflammatory cell Progenitors after Inhaled Allergen in Asthmatic Subjects", Am J. Respir. Crit Care Med., vol. 157, pp. 99-105, 1998.

Mark D. Inman, et al., "Allergen-Induced Increase in Airway Responsiveness, Airway Eosinophilia, and Bone-Marrow Eosinophil Progenitors in Mice", Am. J. Respir. Cell Mol. Biol., vol. 21, pp. 473-479, 1999.

Warren S. Alexander, et al., "The Role of Suppressors of Cytokine Signaling (SOCS) Proteins in Regulation of the Immune Response", Annu. Rev. Immunol. 2004, pp. 503-529; C1-C4; Contents v-vii.

\* cited by examiner

ECKLONIA CAVA EXTRACTS FOR ALLEVIATING OR PREVENTING ASTHMATIC REACTIONS

FIELD OF THE INVENTION

The present invention relates to utilization of *Ecklonia cava* (EC) extracts for reducing asthmatic reactions, and, more particularly, to a method for alleviating or preventing asthmatic reactions such as airway hyperresponsiveness (AHR), airway inflammation, etc., by utilizing *Ecklonia cava* extracts.

BACKGROUND OF THE INVENTION

Asthma is an inflammatory disease that is characterized by bronchial hyperresponsiveness, which can lead to life-threatening airway obstructions and be the cause of symptoms such as wheezing, feeling difficulty in breathing (particularly when air is being exhaled) and feeling tight in the chest. Triggers of an asthmatic attack include rapid changes in temperature or humidity, allergies, upper respiratory infections, drastic exercises, stresses and heavy smoking.

Among the above triggers, inhaled allergens resulting in an immune response are understood as one of the most usual factors. In an asthmatic, inhaled allergens that came to the inner airway are ingested by a type of cell known as an antigen presenting cell. An antigen presenting cell then presents pieces of the allergens to another immune cell, for example, a T helper cell, which is a kind of white blood cell helping a human body fight off certain infections. In a healthy person, such an immune cell checks but usually ignores the allergen molecules. In an asthmatic, however, these cells are transformed into a different type of cell such as T helper 2 (Th2). The resultant Th2 cell activates an important arm of the immune system (e.g., the humoral immune system). The humoral immune system produces antibodies against the inhaled allergens. Later, when the asthmatic inhales the same allergens, these antibodies recognize it and activate a humoral response. As a result, chemicals are produced that cause the airway to constrict and release more mucus, and the cell-mediated arm of the immune system is activated.

During an asthmatic episode, an inflamed airway reacts to environmental triggers such as smoke, dust, or pollen. The airway becomes narrow and produces excessive mucus, making it difficult to breathe. In essence, asthma is the result of an immune response in the bronchial airway.

To be more specific, Th2-type cytokine interleukins-4 (IL-4), IL-5 and IL-13 generated by activated $CD4^+$ T cells play a central role in asthmatic pathogenesis, by controlling the key process of immunoglobulin E (IgE) production, growth of mast cells, and differentiation and activation of both mast cells and eosinophils, wherein $CD4^+$ T cells helping B cells make antibodies in response to challenge. Genetic and environmental factors influence the development of Th1 or Th2 cells. The direction of the differentiation of Th cells is determined by the cytokine environment at the site of initial antigenic activation. It has been well known that the presence of IL-4 during the induction phase leads to the predominance of Th2 cells, which subsequently determine the allergic inflammatory responses as described above. Th2 cells are the predominant lymphocyte population that infiltrates the airway of an asthmatic. Moreover, the cytokine products of Th2 cells perform essential roles in airway eosinophilia, airway hyperresponsiveness, and serum IgE production.

Eosinophils are generated in the bone marrow, and recent observations on both mice and humans indicate that pulmonary allergen exposure results not only in an increased output of eosinophils from hemopoietic tissues but also in an increased migration of Th2 cells to the lung. It is the accumulation of activated eosinophils during the late phase response to the allergen exposure that ultimately induces progressive inflammatory tissue damage. Thus, inhibiting Th2 cytokines via the augmentation of Th1 cytokine production may prove useful for treatment of allergic asthma.

In the meantime, suppressor of cytokine signalling (SOCS) is a molecule that functions as a negative regulator of cytokine signaling. SOCS is known to be involved in the pathogenesis of a host (e.g., an animal or a human) that suffers from inflammatory diseases. The discovery of SOCS proteins has provided novel insights into the cytokine regulation of Th1 and Th2 immune responses. Eight members of the SOCS protein family have been identified as follows: cytokine-inducible src homology 2 (SH2) domain-containing proteins and SOCS-1 to SOCS-7.

Among the SOCS proteins, SOCS-3 is expressed preferentially in Th2 cells and plays a crucial role in regulation of the onset and maintenance of Th2-mediated allergic diseases. The concentration of serum IgE is also increased in an asthmatic, and this can be interpreted as an evidence of high SOCS-3 expression. On the other hand, SOCS-5 is expressed preferentially in Th1 cells, and its expression can result in reduction of Th2 differentiation due to the inhibition of IL-4 signaling.

Therefore, the inhibition of SOCS-3 expression may be a useful therapeutic approach to the treatment of Th2-dominant diseases, including allergic asthma.

SUMMARY OF THE INVENTION

It is, therefore, a primary object of the present invention to utilize *Ecklonia cava* extracts to alleviate or prevent asthmatic reactions, such as airway hyperresponsiveness, airway inflammation, etc., by inhibiting SOCS-3 expression and suppressing the pathogenetic process of asthma.

In accordance with an aspect of the present invention, a method of alleviating or preventing inflammation in an animal is provided. In concrete, the method comprises the step of administering to an animal a composition including an *Ecklonia cava* extract in an amount effective to suppress SOCS-3 expression in the animal to thereby alleviate or prevent inflammation in the animal.

BRIEF DESCRIPTION OF THE DRAWINGS

The above object and features of the present invention will become apparent from the following description of the preferred embodiments given in conjunction with the accompanying drawings, in which.

DETAILED DESCRIPTION OF THE PREFERRED EMBODIMENTS

In the following detailed description, reference is made to the accompanying drawings that show, by way of illustration, specific embodiments in which the invention may be practiced. These embodiments are described in sufficient detail to enable those skilled in the art to practice the invention. It is to be understood that the various embodiments of the invention, although different, are not necessarily mutually exclusive. The following detailed description is, therefore, not to be taken in a limiting sense, and the scope of the present invention is defined only by the appended claims that should be appropriately interpreted along with the full range of equivalents to which the claims are entitled.

Then, experiments performed for better understanding the present invention will be described in detail as follows, which are set forth to illustrate, but are not to be construed to limit the present invention.

Materials and Methods for Practicing the Present Invention

First, a process for preparing *Ecklonia cava* extracts that are essential in practicing the present invention will be now described in detail.

*Ecklonia cava* is a brown alga (Laminariaceae), which is found abundant in the subtidal regions of the Cheju Island, Korea. Recently, an increasing number of evidences have demonstrated that *Ecklonia cava* exhibits radical scavenging activity, matrix metalloproteinase inhibitory activity, bactericidal activity, protease inhibitory activity, antioxidative activity, anti-inflammatory activity, etc.

According to the present invention, the material for alleviating or preventing asthmatic reactions is extracted and purified as follows.

*Ecklonia cava* was collected along the Cheju Island coast of Korea during the period from October 2004 to March 2005. *Ecklonia cava* was washed three times with tap water to remove impurities, e.g., salt, epiphytes, sand, etc., which were attached to the surface of *Ecklonia cava*. Then, it was stored at $-20°$ C. The frozen *Ecklonia cava* samples were lyophilized and homogenized by using a grinder before extraction. Finally, the powdered *Ecklonia cava* was immersed in an organic solvent to obtain *Ecklonia cava* extracts. Useful in this extraction is an organic solvent which is preferably selected from the group consisting of methanol, ethanol, ethyl acetate, acetonitrile, acetone, water and a mixture thereof and water/ethanol mixture. Optionally, said extraction procedure may be repeated at least twice in order to increase the yield thereof, wherein a different organic solvent may be used at each repetitive step.

In the present invention, the dried *Ecklonia cava* powder of 1 kg is extracted with, e.g., 95% EtOH (1:10 w/v) and evaporated in vacuo. To eliminate undesired materials and the remaining solvent from the extracts, use can be made of separation and concentration instruments such as a centrifuge and a rotary evaporation concentrator.

Secondly, animals used for the experiments in accordance with the present invention will be explained.

Female BALB/c mice were obtained from the Charles River Laboratories (Yokohama, Japan), wherein BALB/c is an albino strain of laboratory mouse, and subsequently were kept in an animal facility for at least 1 week before use. All experimental animals used in the present invention were maintained under a protocol approved by the Institutional Animal Care and Use Committee of the Inje University Medical School. All mice were 6-8 weeks old, and the average of the body weights of all mice was 20 g.

Hereinafter, immunization and challenge for the aforementioned mice will be described.

Mice were immunized intraperitoneally with 20 μg of OVA plus 1.0 mg aluminium hydroxide adjuvant on days 1 and 15. Mice were challenged via the airway with OVA of 50 mg/ml in saline every day from days 22 to 24. Control mice were exposed to aerosolized saline. Aerosolization was performed for 20 minutes by placing mice in a chamber having a volume of 15 cm (length)×25 cm (width)×15 cm (height) connected to the ultrasonic nebulizer (NE-U12, Omron, Tokyo, Japan). Mice were injected intraperitoneally with 20 mg/kg/day of OVA in 200 μl of *Ecklonia cava* extracts every day from days 16 to 20.

Then, bronchoalveolar lavage and cell counting were performed as follows.

Mice were anaesthetized and the trachea was cannulated while the thorax gently being massaged. Lungs were lavaged with phosphate buffered saline (PBS) of 0.7 ml. The bronchoalveolar lavage fluid samples were collected and the number of cells in a 50 μl aliquot was determined by using a haemocytometer, wherein the haemocytometer is a glass slide with a chamber for counting blood corpuscles in a given volume. The remaining samples were centrifuged, and the supernatant was stored at $-70°$ until assay of cytokines. The pellet was resuspended in PBS. Cytospin preparations of bronchoalveolar lavage cells were stained with Diff-Quik (International Reagents Corp., Kobe, Japan), which is a commercial stain commonly used for histological staining (i.e., to rapidly stain and differentiate a variety of smears). Two independent, blinded investigators, who were not associated with the present invention, counted the cells, using a microscope. Approximately 400 cells were counted in each of four different random locations.

Next, cytokine assay performed in the present invention will be described.

The cytokine levels in bronchoalveolar lavage fluid were determined by enzyme-linked immunosorbent assay (ELISA), wherein ELISA is a biochemical technique used mainly in immunology to detect the presence of an antibody or an antigen in a sample. The ELISA kits from R&D Systems (Minneapolis, Minn.) were employed for the measurement of IL-4, IL-5, IFN-γ and TNF-α, wherein IFN and TNF stand for interferon and tumor necrosis factor, respectively.

Subsequently, it will be explained in detail how to determine airway hyperresponsiveness.

Airway hyperresponsiveness was measured 3 days after the last OVA challenge on mice in an unrestrained conscious state, according to the method of Hamelmann et al. Mice were placed in a barometric plethysmographic chamber (All Medicus Co., Seoul, Korea), and baseline readings were taken and averaged for 3 minutes. Aerosolized methacholine (Mch) of increasing concentrations (e.g., from 2.5 to 50 mg/ml) was then nebulized through an inlet of the main chamber for 3 minutes, readings were taken and averaged for 3 minutes after each nebulization. The bronchopulmonary resistance is expressed as enhanced pause (Penh), which is calculated by the formula of [expiratory time (Te)/relaxation time (RT)−1]×[peak expiratory flow (PEF)/peak inspiratory flow (PIF)], according to the manufacturers protocol. In the following, the increase in percentage of Penh following challenge, in accordance with various concentrations of methacholine, will be provided, wherein the baseline Penh (after saline challenge) is expressed as 100%.

Hereinafter, histological studies in accordance with the present invention will be explained.

48 hours after the last challenge, lungs were removed from the mice after they had been sacrificed. Prior to the removal of the lungs, the lungs and trachea were filled intraperitoneally with a fixative of 4% paraformaldehyde by using a ligature around the trachea. Lung tissues were fixed with 10% (v/v) paraformaldehyde. The specimens were dehydrated and embedded in paraffin. For histological examination, 4 μm sections of fixed embedded tissues were cut on a Leica model 2165 rotary microtome (Leica, Nussloch, Germany), placed on glass slides, deparaffinized and sequentially stained with both hematoxylin 2 and eosin-Y (Richard-Allan Scientific, Kalamazoo, Mich.). An inflammation score was graded by three independent investigators who were not associated with the present invention.

Then, the western blot analysis performed in the present invention will be described.

The western blot (alternately, immunoblot) is a method to detect a specific protein in a given sample of tissue homogenates or extracts. It uses gel electrophoresis to separate native or denatured proteins by the length of the polypeptide or by the 3-D structure of the protein. The proteins are then transferred to a membrane (typically nitrocellulose or PVDF), where they are probed or detected by using antibodies specific to the target protein.

In the present invention, the lung tissues were homogenized, washed with PBS, and incubated in lysis buffer in addition to a protease inhibitor cocktail (Sigma, St. Louis, Mo.) to obtain extracts of lung proteins. The samples were loaded to 10% Sodium dodecyl sulfate-polyacrylamide gel electrophoresis (SDS-PAGE) gels and were electrotransferred to nitrocellulose, wherein SDS-PAGE is a technique for separating denatured proteins in an electrical field. The blots were incubated with the appropriate concentration of specific antibodies. After being washed, the blots were incubated with horseradish peroxidase-conjugated second antibodies. The membranes were stripped and reblotted with anti-actin antibodies (Sigma) to confirm the equal loading of proteins in each lane.

Next, measurement of the levels of OVA-specific serum IgE will be explained.

The levels of OVA-specific serum IgE were determined by means of ELISA, by using samples collected 12 hours after the last OVA challenge, as mentioned before. In brief, a 96 well microtiter plate was coated with OVA of 10 mg/ml, and then treated with mouse sera followed by anti-mouse IgE of a biotin-conjugated rat (pharmingen, San Diego, Calif.). Then, an avidin-horseradish peroxidase solution was added to each well. Units are optical density readings at a wave length of 405 nm.

Hereinafter, zymography carried out in the present invention will be illustrated.

Gelatin zymography was used to assess the activity of matrix metalloproteinase-9. The supernatant was diluted three times with non-reducing loading buffer (400 mmol/L Tris-HCL, 5% sodium dodecyl sulfate, 20% glycerol, 0.006% bromophenol blue). Fifteen microliters of each of the samples was mixed with the loading buffer, and proteins were separated by polyacrylamide gel electrophoresis at a distance of 0.75 mm under a constant current of 20 mA, wherein an 8% sodium dodecyl sulfate solution with 1% gelatin (Bio-Rad) was used. The gels were incubated in renaturing buffer (i.e., 2.5% Triton X-100 buffer) for 30 minutes to remove the sodium dodecyl sulfate. After being rinsed, the gels were incubated at 37° C. for 20 hours in an enzyme activation buffer (50 mmol/L Tris-HCL [pH 7.3], 200 mmol/L NaCl, and 0.02% Tween 20). The gels were then stained with Coomassie brilliant blue R250 stain and destained with 5% methanol, 7% acetic acid in a PBS solution, and the gelatinolytic activity was detected as clear bands.

Subsequently, measurement of EPO will be described.

The suspension of bronchoalveolar lavage cells and the pulmonary homogenates were frozen/thawed three times by using liquid nitrogen and a water bath at 37° C. to obtain EPO. The bronchoalveolar lavage fluid was centrifuged at 4° C. for 10 minutes and serially diluted in a 96-well plate (75 μl/well) followed by the addition of 150 μl of substrate (1.5 mM o-phenylenediamine and 6.6 mM $H_2O_2$ in 0.05 M Tris-HCl, pH 8.0). After 30 minutes at room temperature, the reaction was stopped by the addition of 75 μl of 30% $H_2SO_4$, and the absorbance of the samples was determined to be 492 nm on an ELISA reader.

Lastly, densitometric analysis and statistics carried out in the present invention will be explained.

All immunoreactive signals were analyzed by means of densitometric scanning (Gel Doc XR; Bio-Rad, Hercules, Calif.). Data were expressed as mean±SEM. Statistical comparisons were performed by using one-way analysis of variance (ANOVA) followed by the Fisher's test, which is well known for providing a statistical test of independence and is being frequently used in medical research. Significant differences between 2 groups were determined by using the unpaired Student's t test adopting a statistical method analogous to the calculation of the normal deviation. Statistical significance was set at $P<0.05$.

Based upon the experiments described above, it is believed that a composition comprising *Ecklonia cava* extracts may be included in foods, dietary supplements or nutraceuticals for alleviation or prevention of asthmatic reactions. One skilled in the art can use the results of experiments in cells and animals described above to determine effective amounts to be administered to other animals, including humans. By "effective amount," it is meant a concentration that inhibits allergic asthma either in vitro in cells or in vivo in animals. For example, human test doses can be extrapolated from effective doses in cell studies or from effective doses in vivo by extrapolating on a body weight or surface area basis. Such extrapolations are routine in the art. A composition comprising *Ecklonia cava* extracts can be formulated for administration as a food supplement by using one or more fillers. Alternatively, a composition comprising these extracts can be administered as conventional pharmaceuticals by using one or more physiologically acceptable carriers or excipients. A nutraceutical composition can be formulated for administration by any route including, but not limited to, inhalation or insufflation (through mouth or nose), oral, buccal, parenteral, vaginal, or rectal administration. In one embodiment, oral administration, the composition is added directly to foods and ingested as part of a normal meal. Various methods are known to one skilled in the art for addition or incorporation of nutraceuticals into foods.

A composition for use in the present invention can also be administered in the form or tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising *Ecklonia cava* extracts can also be coated by methods well known in the art. Liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill and are listed in places such as the U.S. Pharmacopeia. In one embodiment, the oral preparation is formulated to provide controlled time release of the active nutraceutical components. For oral administration, *Ecklonia cava* extracts can be formulated as a tablet or lozenge.

For administration by inhalation, a composition for use in the present invention can be delivered in the form of an aerosol spray in a pressurized package or as a nebulizer, with use of suitable propellants. In the case of a pressurized aerosol, the dosage unit can be determined by providing a valve to deliver a metered dose.

A parenterally administered composition is formulated to allow for injection, either as a bolus or as a continuous infusion. Formulations for injection can be prepared in unit dosage forms, such as ampules, or in multi-dose units, with added preservatives. The composition for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia.

For rectal administration or vaginal administration, a composition for use in the present invention can be formulated as suppositories, creams, gels, or retention enemas.

For dietary supplements, *Ecklonia cava* extracts can be added in concentrations up to 5% by weight and mixed according to methods routine in the art. Dietary supplements for animals can be prepared in a variety of forms including, but not limited to, liquid, powder, or solid pill forms. In the present invention, *Ecklonia cava* extracts can be administered either alone or in combination with other phytochemicals known to affect asthmatic reactions, where combining compounds or extracts would lead to synergistic effects.

Accordingly, it is believed that a combination diet of dietary supplement comprising *Ecklonia cava* extracts and at least one other phytochemical will also be useful to alleviate or prevent asthmatic reactions in animals, including humans.

Effects from Practicing the Present Invention with the Above Materials and Methods Next, the effects from practicing the present invention with the above materials and methods will be described in further detail, with reference to the accompanying drawings.

Figure 1:
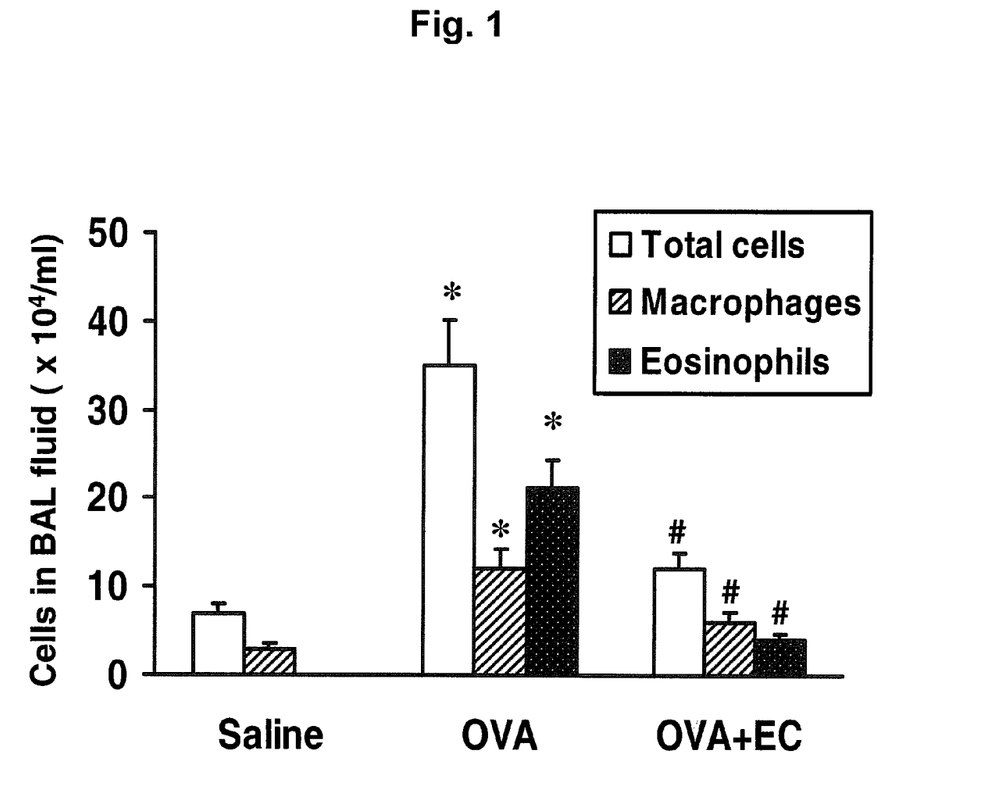
FIG. 1 is a graph showing the experimental result in accordance with the present invention exhibiting how *Ecklonia cava* extracts affect the recruitment of inflammatory cells in bronchoalveolar lavage (BAL) fluid on mice suffering from ovalbumin-induced (OVA-induced) allergic asthma.

FIG. 1 is a graph showing the experimental result in accordance with the present invention exhibiting how *Ecklonia cava* extracts affect the recruitment of inflammatory cells in bronchoalveolar lavage (BAL) fluid on mice suffering from ovalbumin-induced (OVA-induced) allergic asthma.

Referring to FIG. 1, mice were treated with saline, OVA-inhaled mice were administered with saline, and OVA-inhaled mice were administered with *Ecklonia cava* extracts of 40 mg/kg (i.e., OVA+EC extracts), respectively. Bronchoalveolar lavage cells were separated by using a Cytospin, and then stained with Diff-Quik as described above. Differential cell counting was performed by using standard morphological criteria. The bronchoalveolar lavage cells were collected 2 days after the last OVA challenge. The experimental results were obtained from one representative experiment out of 5 experiments performed. In this experiment, 5 mice were used (n=5). Statistical significance was set at $*p<0.05$ vs. saline-treated mice and $\#p<0.05$ vs. OVA-treated mice.

The number of the total cells in bronchoalveolar lavage fluid 2 days after the final OVA challenge in the murine asthmatic was significantly increased by approximately 5-fold, compared with the number of the total cells on the saline-exposed control mice, as shown in FIG. 1. OVA sensitization and challenge also induced predominant increases in normal eosinophils within the bronchoalveolar lavage fluid. The number of eosinophils in the bronchoalveolar lavage fluid on the OVA-exposed mice was significantly increased, while the number of eosinophils on the mice treated with *Ecklonia cava* extracts was remarkably reduced. Thus, it could be admitted that *Ecklonia cava* extracts reduced the increased number of inflammatory cells in the bronchoalveolar lavage fluid of OVA-sensitized and OVA-challenged mice. In addition, this effect was associated with some degree of inhibition in lung eosinophilia.

Figure 2:
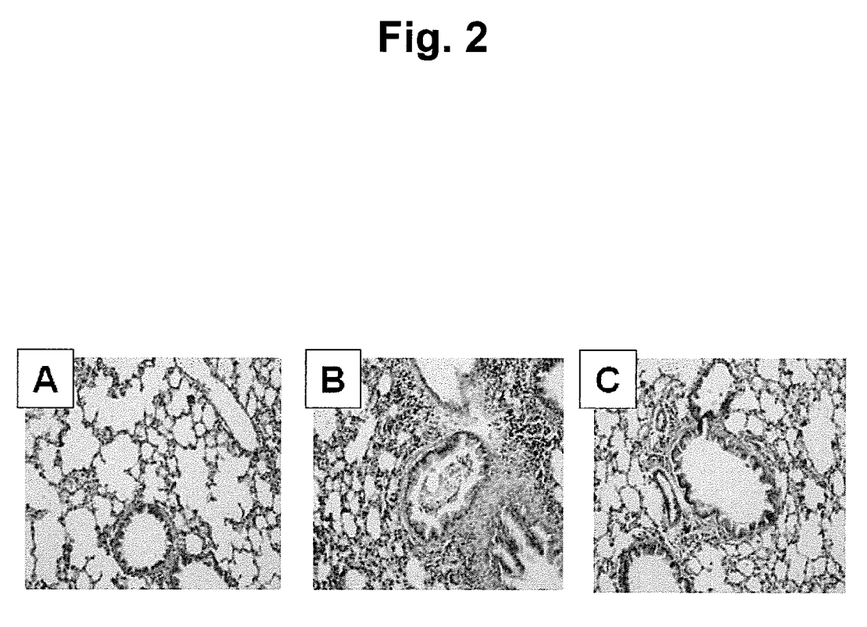
FIG. 2 depicts pathological changes in lung tissues of OVA-sensitized and OVA-challenged mice in accordance with the present invention.

FIG. 2 depicts pathological changes in lung tissues of OVA-sensitized and OVA-challenged mice in accordance with the present invention.

Mice were sensitized and challenged as shown in FIG. 1. Referring to FIG. 2, sections were obtained from the lungs of mice which were treated with saline (A), OVA-inhaled mice administered with saline (B), and OVA-inhaled mice administered with *Ecklonia cava* extracts of 40 mg/kg (OVA+EC extracts) (C), respectively. The lungs were removed 2 days after the last airway challenge. Sections were stained by haematoxylin and eosin staining (×200). 6 animals were assigned to each group of mice.

The results of histological examination of lung tissues paralleled the number of the cells in the bronchoalveolar lavage fluid. Marked influx of inflammatory cells into the airway and around the blood vessels was detected on the OVA-sensitized and OVA-challenged mice (B), but not on the saline-treated control mice (A), as shown in FIG. 2. On mice treated with *Ecklonia cava* extracts (C), significant reduction in the infiltration of inflammatory cells within the peribronchiolar and perivascular regions was shown as in FIG. 2. Mucus hypersecretion and airway occlusion were the prominent histopathological features of the murine asthmatic lung. Both mucus cell hypertrophy and airway luminal narrowing caused by secreted mucus were observed on the OVA-sensitized and OVA-challenged mice (B). Further, it could be found that the administration of *Ecklonia cava* extracts might lead to remarkable improvement of luminal narrowing in the airway on mice treated with *Ecklonia cava* extracts (C), as shown in FIG. 2. These results indicate that *Ecklonia cava* extracts turns on pathological changes of OVA-induced asthma, that is, *Ecklonia cava* extracts are very capable of inhibiting the development of the allergic state caused by OVA-induced asthma on mice.

Figure 3:
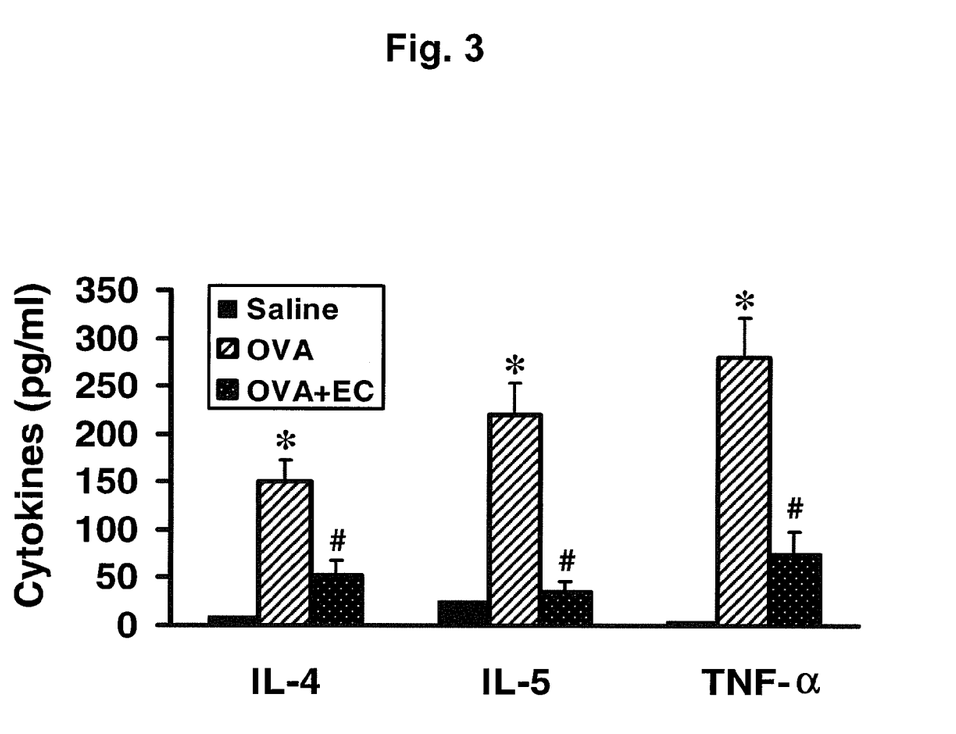
FIG. 3 is a graph showing the experimental result in accordance with the present invention exhibiting how *Ecklonia cava* extracts affect the levels of IL-4, IL-5, and TNF-α.

FIG. 3 is a graph showing the experimental result in accordance with the present invention exhibiting how *Ecklonia cava* extracts affect the levels of IL-4, IL-5, and TNF-α.

OVA-sensitized mice were treated as mentioned before. Bronchoalveolar lavage was performed 2 hours after the last airway challenge. Data were expressed as means±SEM from 5 independent experiments on the response in 5-7 animals. Statistical significance was set at *$p<0.05$ vs. saline-treated mice and #$p<0.05$ vs. OVA-treated mice.

As mentioned earlier, Th2 cytokines, IL-4 and IL-5 play important roles in the initiation and propagation of allergic inflammatory responses. Also, the results of several studies have suggested that TNF-α performs an important function in asthma pathogenesis. TNF-α can induce lung neutrophil infiltration, and some asthmatics show elevated levels of serum TNF-α. In order to determine whether pretreatment with *Ecklonia cava* extracts affects cytokine secretion in the bronchoalveolar lavage fluid, the levels of IL-4, IL-5, and TNF-α were determined by means of ELISA. The bronchoalveolar lavage fluid was obtained 4 hours after the final airway challenge. The levels of IL-4, IL-5 and TNF-α in the bronchoalveolar lavage fluid were significantly increased on the OVA-challenged mice, when compared with those on the saline-treated control mice. The administration of *Ecklonia cava* extracts reduced the concentrations of IL-4 and IL-5 by 66% and 84%, respectively, and resulted in a 73% reduction in the secretion of TNF-α, as shown in FIG. 3. *Ecklonia cava* extracts enhanced IFN-γ production, but not to a significant degree.

Figure 4:
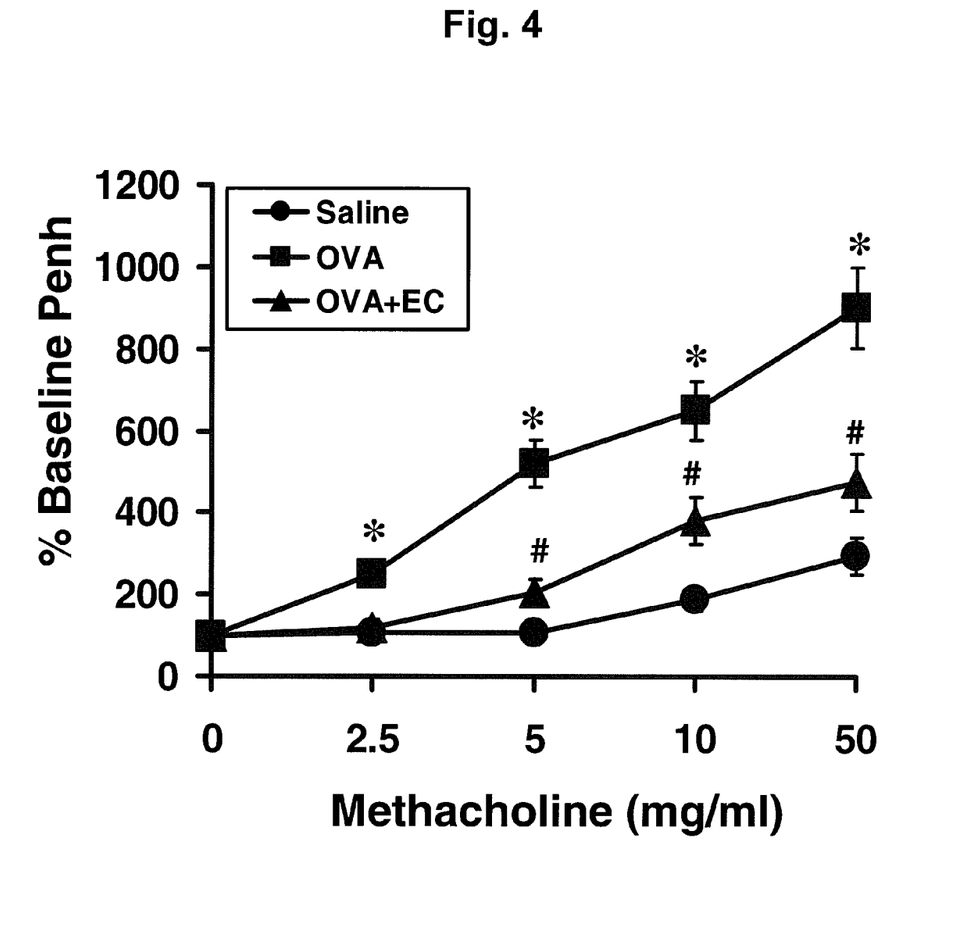
FIG. 4 is a graph showing the experimental result in accordance with the present invention exhibiting how *Ecklonia cava* extracts affect airway responsiveness on OVA-sensitized and OVA-challenged mice.

FIG. 4 is a graph showing the experimental result in accordance with the present invention exhibiting how *Ecklonia cava* extracts affect airway responsiveness on OVA-sensitized and OVA-challenged mice.

Airway responsiveness was measured 72 hours after the last airway challenge. *Ecklonia cava* extracts were administered intraperitoneally from last sensitization to 1 day before the first airway challenge. Airway responsiveness to aerosolized methacholine was measured on unrestrained, conscious mice. Mice were placed into the main chamber and were nebulized first with saline, then with increasing doses (2.5 to 50 mg/ml) of methacholine for 3 minutes per nebulization, Readings of breathing parameters were taken for 3 minutes after each nebulization, during which Penh values were determined. Data were expressed as mean±SEM from 6 independent experiments. Statistical significance was set at *$p<0.05$ vs. saline-treated mice and #$p<0.05$ vs. OVA-treated mice.

To be more specific, airway responsiveness was assessed as percent increases of Penh in response to increasing doses of methacholine. The dose-response curve of percent Penh on the OVA-sensitized and OVA-challenged mice was shifted as shown in FIG. 4. That is, the percent Penh generated by methacholine administration (at doses from 2.5 to 50 mg/ml) was significantly increased on the OVA-sensitized and OVA-challenged mice, compared with that on the control mice. On the OVA-sensitized and OVA-challenged mice treated with *Ecklonia cava* extracts, however, the dose-response curve of percent Penh was shown to be shifted to the right, compared with that on the OVA-sensitized and OVA-challenged mice that were not treated with *Ecklonia cava* extracts (clearly, this shift was dose-dependent). These results show that treatment with *Ecklonia cava* extracts reduces OVA-induced airway responsiveness to methacholine.

Figure 5:
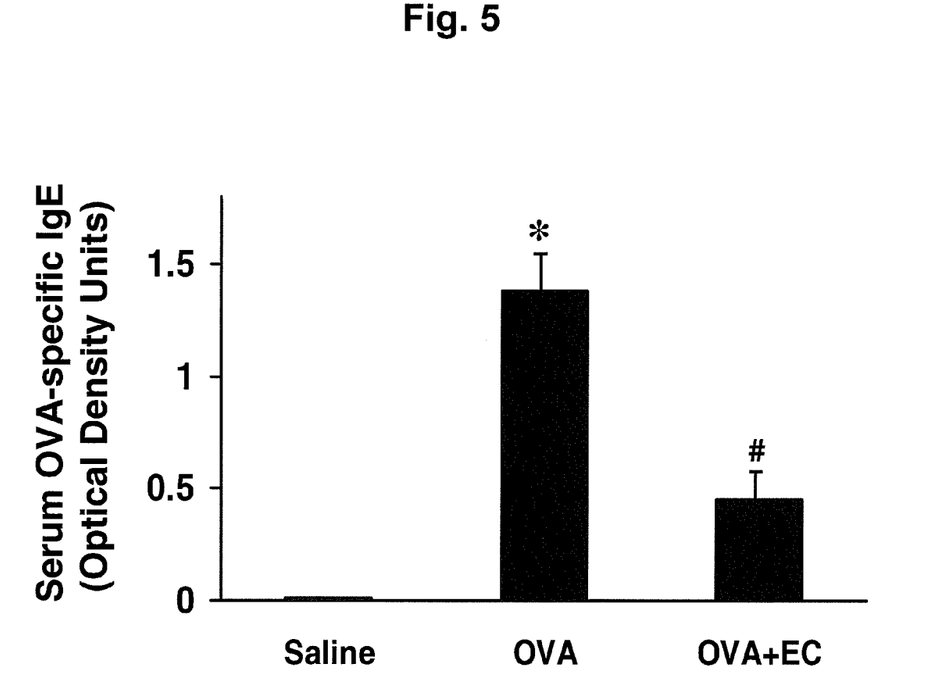
FIG. 5 is a graph showing the experimental result in accordance with the present invention exhibiting how *Ecklonia cava* extracts affect the level of serum OVA-specific IgE antibodies.

FIG. 5 is a graph showing the experimental result in accordance with the present invention exhibiting how *Ecklonia cava* extracts affect the level of serum OVA-specific IgE antibodies.

Mice were sensitized and challenged as described above. The levels of OVA-specific IgE were measured 12 hours after the last airway challenge. Blood was collected by cardiac puncture for measurement of OVA-specific IgE by means of ELISA. *Ecklonia cava* extracts were administered intraperitoneally from last sensitization to 1 day before the first airway challenge. Statistical significance was set at *$p<0.05$ vs. saline-treated mice and #$p<0.05$ vs. OVA-treated mice.

The cross-linking of allergen-specific IgE on the surfaces of mast cells upon allergen challenge was related to the initiation of the early asthmatic reaction. The serum levels of OVA-specific IgE were measured 12 hours after the final airway challenge. It was determined that sensitization and challenge with OVA resulted in increased serum levels of OVA-specific IgE, while the serum levels on the saline-treated control mice were low. The treatment of sensitized mice with *Ecklonia cava* extracts resulted in a 67% reduction in OVA-specific IgE, as shown in FIG. 5. These results may be a support for the conclusion that *Ecklonia cava* extracts suppress the generation of a Th2-type immune response in the murine asthmatic.

Figure 6:
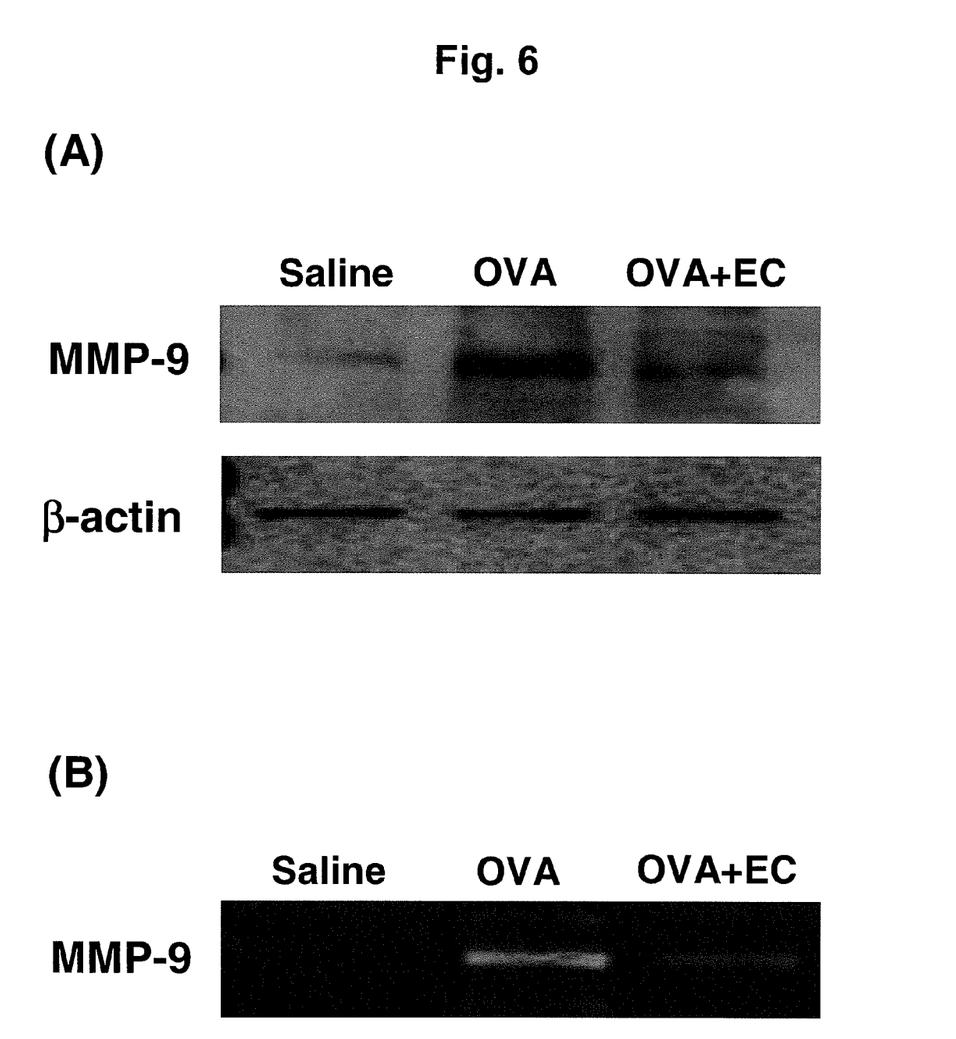
FIGS. 6A and 6B illustrate the experimental result in accordance with the present invention showing how *Ecklonia cava* extracts affect the expression of matrix metalloproteinase-9 (MMP-9) in the lungs of OVA-challenged mice.

FIGS. 6A and 6B illustrate the experimental result in accordance with the present invention showing how *Ecklonia cava* extracts affect the expression of matrix metalloproteinase-9 (MMP-9) in the lungs of OVA-challenged mice.

Matrix metalloproteinases belong to a family of zinc-dependent and calcium-dependent endopeptidases that are capable of proteolytically degrading many of the components of the extracellular matrix. Matrix metalloproteinases are generated not only by structural cells such as fibroblasts, endothelial cells, and epithelial cells, but also by inflammatory cells including macrophages, lymphocytes, neutrophils, and eosinophils. Metalloproteinase-9 may play a role in chronic airway inflammation, including the induction of migration of eosinophils, lymphocytes, and neutrophils across basement membranes, thereby remodeling the chronic inflammatory process in an asthmatic.

OVA-sensitized mice might be pretreated or not with *Ecklonia cava* extracts before OVA challenge. The cell extracts were prepared from the lungs of the OVA-treated mice 48 hours after challenge, and also prepared from the lung tissues of saline-treated mice. Referring to FIGS. 6A and 6B, the extracts were subject to immunoblot analysis with anti-actin antibodies (Beta) to confirm the equal loading of proteins in each lane to metalloproteinase-9 (A). Sampling was performed 48 hours after challenge with the saline, OVA, or OVA plus *Ecklonia cava* extracts, and then analyzed by zymography (B). Data were expressed as mean±SEM from 6 independent experiments.

Referring to FIGS. 6A and 6B, it could be noted that challenge with OVA resulted in remarkable induction of metalloproteinase-9 activity in bronchoalveolar lavage fluid, while this result could not be observed on the control mice. The administration of *Ecklonia cava* extracts prior to the final airway OVA challenge resulted in the significant inhibition of metalloproteinase-9 expression in the lung tissues as shown in FIG. 6A, as well as the decrease of the level of metalloproteinase-9 gelatinolytic activity in the bronchoalveolar lavage fluid as shown in FIG. 6B. These results indicate that *Ecklonia cava* extracts regulate metalloproteinase-9 expression.

Figure 7:
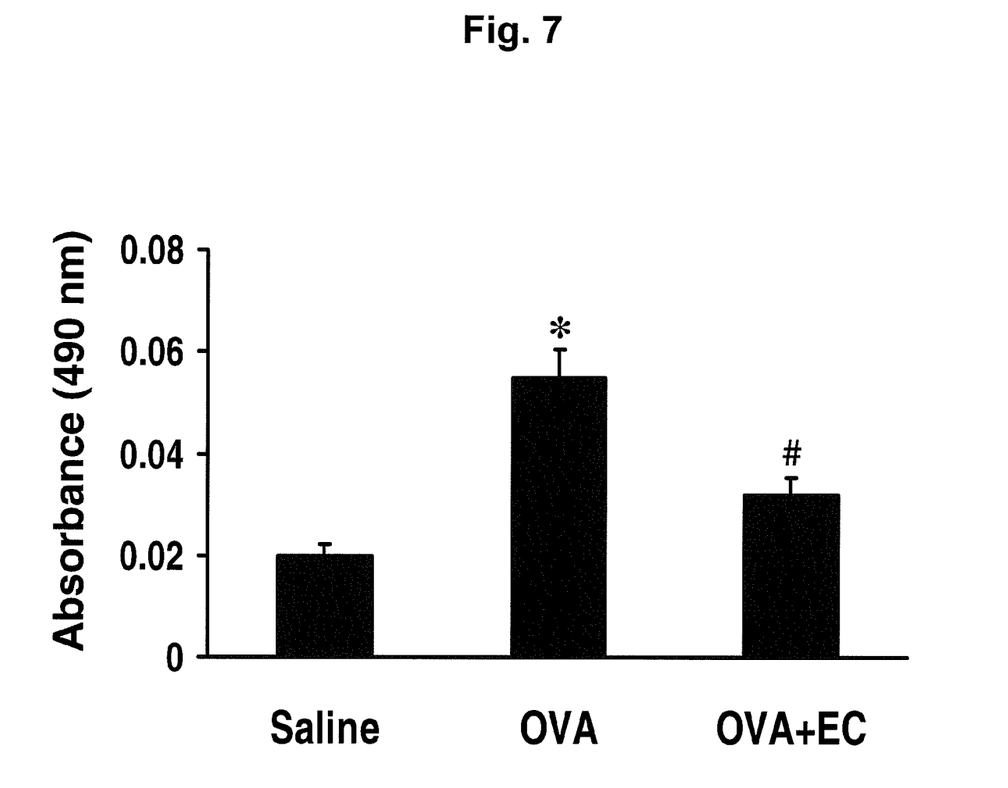
FIG. 7 is a graph showing the experimental result in accordance with the present invention exhibiting how *Ecklonia cava* extracts affect the level of eosinophil peroxidase (EPO) content in bronchoalveolar lavage fluid on OVA-sensitized and OVA-challenged mice.

FIG. 7 is a graph showing the experimental result in accordance with the present invention exhibiting how *Ecklonia cava* extracts affect the level of eosinophil peroxidase (EPO) content in bronchoalveolar lavage fluid on OVA-sensitized and OVA-challenged mice.

Mice were sensitized and challenged as described above. EPO activity was measured in bronchoalveolar lavage fluid 48 hours after the last airway challenge. *Ecklonia cava* was administered intraperitoneally from last sensitization to 1 day before the first airway challenge. Data were expressed as mean±SEM from 6 independent experiments. Statistical significance was set at *$p<0.05$ vs. saline-treated mice and #$p<0.05$ vs. OVA-treated mice.

Tissue levels of EPO were well correlated with the number of eosinophils at inflammation sites. According to the number of eosinophils measured in the bronchoalveolar lavage fluid of OVA-challenged mice, as shown in FIG. 7, the EPO levels in bronchoalveolar lavage fluid were significantly increased 24 hours after OVA inhalation, compared with the EPO levels after saline inhalation. The increased levels of EPO were significantly reduced, by approximately 42% upon the administration of *Ecklonia cava* extracts.

Figure 8:
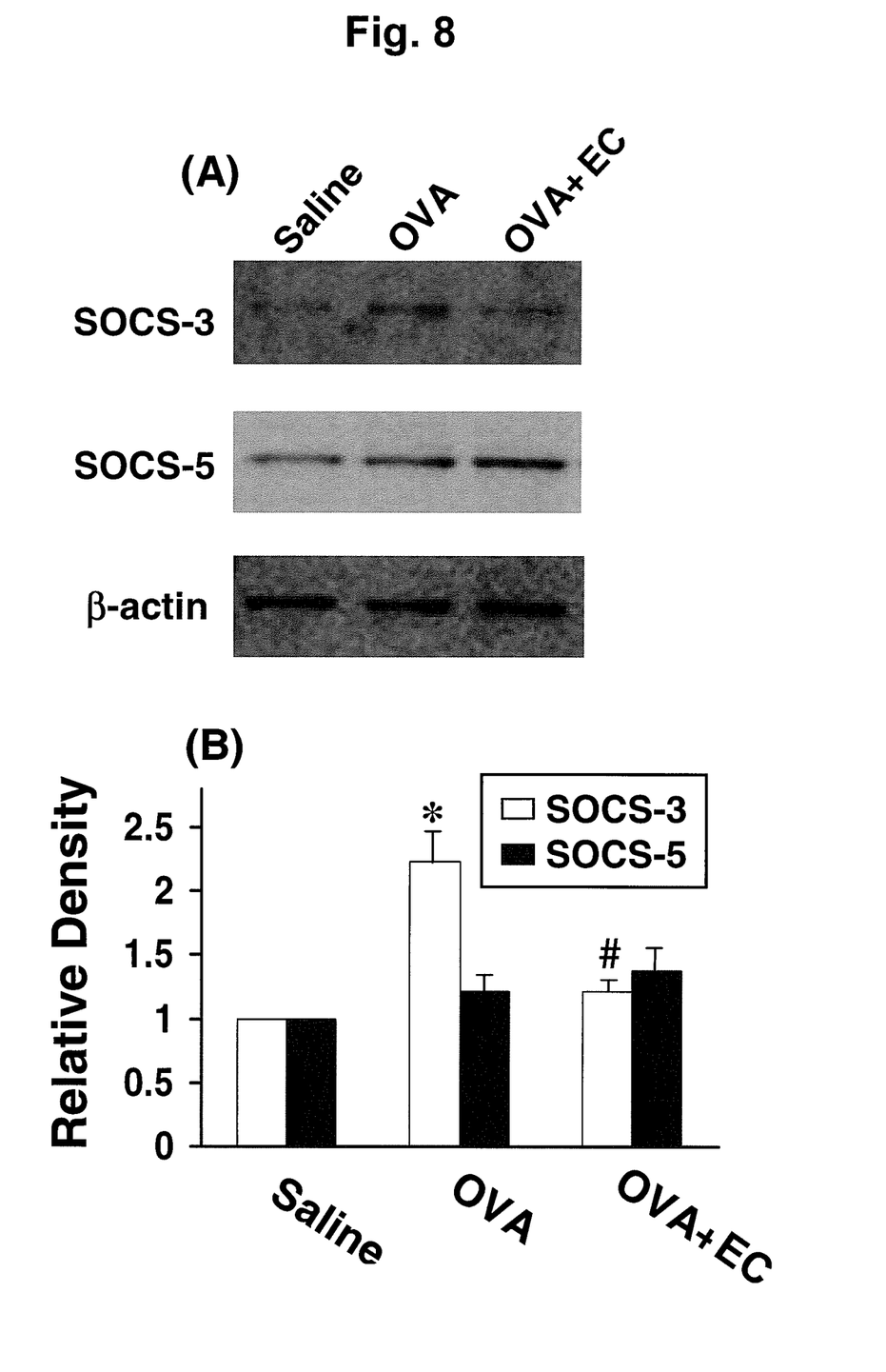
FIGS. 8A and 8B illustrate the experimental result in accordance with the present invention exhibiting how *Ecklonia cava* extracts affect the expression of SOCS-3 and SOCS-5 in lung tissues of OVA-sensitized and OVA-challenged mice.

FIGS. 8A and 8B illustrate the experimental result in accordance with the present invention exhibiting how *Ecklonia cava* extracts affect the expression of SOCS-3 and SOCS-5 in lung tissues of OVA-sensitized and OVA-challenged mice.

There are provided experimental results of the western blotting on SOCS-3 and SOCS-5 in FIG. 8A. Sampling was performed 72 hours after the last challenge on mice administered with saline (Saline), OVA-inhaled mice administered with saline (OVA), and OVA-inhaled mice administered with *Ecklonia cava* extracts by 40 mg/kg (OVA+EC). Densitometric analyses were presented as the relative ratio of the respective molecules to actin, as shown in FIG. 8B. The relative ratio of the respective molecules in the lung tissues of the saline-treated mice was arbitrarily set 1. Data were expressed as mean±SEM from 6 independent experiments. Statistical significance was set at *$p<0.05$ vs. saline-treated mice and #$p<0.05$ vs. OVA-treated mice.

Seeing FIGS. 8A and 8B, SOCS-3 and SOCS-5 are expected to be the principal modulators of allergic immune diseases, and they reciprocally inhibit the processes of Th1 and Th2 differentiation. Therefore, the expression of SOCS-3 and SOCS-5 in lung tissues was assessed by means of the western blot analysis. The western blot analysis showed that the levels of SOCS-3 proteins in lung tissues were significantly increased 48 hours after OVA inhalation, compared with the levels of SOCS-3 proteins after saline inhalation, as shown in FIGS. 8A and 8B. The increased level of the SOCS-3 proteins was reduced as a result of administration of *Ecklonia cava* extracts. However, treatment with *Ecklonia cava* extracts failed to augment SOCS-5 expression. These findings indicate that *Ecklonia cava* extracts could inhibit allergic airway reactions by inhibiting the recruitment of Th2 cells into the airway, rather than the enhancement of a Th1 response.

As described above, *Ecklonia cava* extracts inhibit OVA-induced airway inflammation in a murine asthmatic in accordance with the present invention. The administration of *Ecklonia cava* extracts prior to the final airway OVA challenge resulted in significant inhibition of all asthmatic reactions. In addition, the EC extract-mediated inhibition of asthmatic reactions appears to be contributing to the initial suppression of an allergen-specific IgE response. Besides, *Ecklonia cava* extracts decrease SOCS-3 expression, which increases the risk of Th2-mediated type I allergic disease. Treatment with *Ecklonia cava* extracts was also proved to have an effect on the increase in serum IgE concentrations in an asthmatic showing high SOCS-3 expression.

While the invention has been shown and described with respect to the preferred embodiments, it will be understood by those skilled in the art that various changes and modifications may be made without departing from the spirit and the scope of the invention as defined in the following claims.

What is claimed is:

1. A method of alleviating symptoms of asthma in an animal in need thereof, the method comprising:
   administering to said animal a composition comprising an effective amount of an aqueous ethanol extract of *Ecklonia cava*, wherein said extract of *Ecklonia cava* suppresses expression of cytokine signaling-3 (SOCS-3) to alleviate symptoms of asthma in the animal.

2. The method of claim 1, wherein the composition further comprises a physiologically acceptable carrier.

3. The method of claim 1, wherein the composition is an oral composition.

4. The method of claim 1, wherein the composition is administered to the animal in a food.

5. The method of claim 1, wherein the composition is a nutraceutical.

6. The method of claim 1, wherein the composition is a dietary supplement.

7. The method of claim 1, wherein the composition is in the form of a capsule, a tablet, a lozenge or a coated tablet.

8. The method of claim 1, wherein the composition is in the form of a solution, a syrup, or a suspension.

9. The method of claim 1, wherein the effective amount of the extract of *Ecklonia cava* is 40 mg/kg.

10. The method of claim 1, wherein the symptoms associated with asthma are caused by inhaled allergens.

11. A method of alleviating airway inflammation associated with asthma in an animal in need thereof, the method comprising:
   administering to said animal a composition comprising an effective amount of an aqueous ethanol extract of *Ecklonia cava*, wherein the extract suppresses expression of cytokine signaling-3 (SOCS-3) to alleviate airway inflammation associated with asthma in the animal.

12. The method of claim 11, wherein the therapeutically effective amount of the extract is 40 mg/kg.

13. The method of claim 11, wherein the airway inflammation is caused by inhaled allergens.

14. The method of claim 11, wherein the composition further comprises a physiologically acceptable carrier.

15. The method of claim 11, wherein the composition is administered to the animal in a food.

16. The method of claim 11, wherein the composition is a nutraceutical.

* * * * *